United States Patent [19]

Azuma et al.

[11] 4,440,739
[45] Apr. 3, 1984

[54] RADIOACTIVE DIAGNOSTIC AGENT AND NON-RADIOACTIVE CARRIER THEREFOR

[75] Inventors: Makoto Azuma, Takarazuka; Masaaki Hazue, Amagasaki, both of Japan

[73] Assignee: Nihon Medi-Physics Co., Ltd., Hyogo, Japan

[21] Appl. No.: 324,903

[22] Filed: Nov. 25, 1981

[30] Foreign Application Priority Data

Nov. 27, 1980 [JP] Japan ................................ 55-167135

[51] Int. Cl.³ ..................... A61K 43/00; A61K 49/00
[52] U.S. Cl. ........................................... 424/1.1; 424/9
[58] Field of Search ........................................ 424/1, 9

[56] References Cited

U.S. PATENT DOCUMENTS

| | | | |
|---|---|---|---|
| 3,740,418 | 6/1973 | Rajamani et al. | 424/1 |
| 4,215,045 | 7/1980 | Knapp, Jr. | 424/1 |
| 4,256,726 | 3/1981 | Kato | 424/1 |
| 4,298,591 | 11/1981 | O'Brien, Jr. et al. | 424/1 |

OTHER PUBLICATIONS

Chiotellis et al., Chem. Abstracts, vol. 87 (1977) #98177g.

*Primary Examiner*—Christine M. Nucker

[57] ABSTRACT

A $^{99m}$Tc-labeled radioactive diagnostic agent being useful for visualization and dynamic inspection of hepatobiliary ducts and having a high stability and no material toxicity, which comprises $^{99m}$Tc in the form of pertechnetate and a non-radioactive carrier, the non-radioactive carrier comprising an N-pyridoxyl-α-amino acid of the formula:

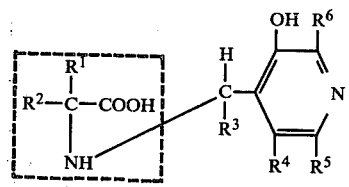

wherein $R^1$ and $R^2$ are each an atom or an atomic group present in the α-amino acid residue encompassed by the dotted line and $R^3$, $R^4$, $R^5$ and $R^6$ are each a hydrogen atom, a halogen atom, a $C_1$–$C_{10}$ alkyl group or a $C_1$–$C_{10}$ alkyl group substituted with at least one hydrophilic group or its salt, and a reducing agent for pertechnetate.

12 Claims, No Drawings

RADIOACTIVE DIAGNOSTIC AGENT AND NON-RADIOACTIVE CARRIER THEREFOR

The present invention relates to a $^{99m}$Tc-labeled radioactive diagnostic agent and a non-radioactive carrier therefor. More particularly, it relates to a novel $^{99m}$Tc-labeled radioactive diagnostic agent being useful for visualization and dynamic inspection of hepatobiliary ducts and having a high stability and no material toxicity, and a non-radioactive carrier therefor.

For the purpose of non-invasive, dynamic inspection of hepatobiliary ducts, there have been used $^{131}$I-labeled radioactive diagnostic agents such as $^{131}$I-labeled bromosulfophthalein ($^{131}$I-BSP) and $^{131}$I-labeled Rose Bengal ($^{131}$I-RB). However, $^{131}$I emits β-ray and has a long half life (i.e. about 8 days) so that those radioactive diagnostic agents result unfavorably in giving remarkable radiation exposure for patients.

Since $^{99m}$Tc emits only γ-ray of about 140 KeV and has a short half life (i.e. about 6 hours), it is quite suitable as a nuclide for radioactive diagnostic agents to be administered to human bodies. Because of this reason, attempts have been made to provide $^{99m}$Tc-labeled radioactive hepatobiliary diagnostic agents, of which examples are $^{99m}$Tc-penicillamine, $^{99m}$Tc-2-mercaptoisobutyric acid, $^{99m}$Tc-N-(2,6-dimethylphenylcarbamoylmethyl)iminodiacetic acid ($^{99m}$Tc-HIDA), etc. However, these conventional radioactive diagnostic agents are not satisfactory in their disappearance rate from the blood, their transfer rate from the liver into the gall bladder, their excretion percentage into the urine, their stability and toxicity, etc.

Recently, it was found that pyridoxylideneaminates labeled with $^{99m}$Tc have excellent properties suitable for diagnosis of hepatobiliary ducts [Kaku Igaku, 14, 927 (1977); J. Nucl. Med., 19, 397 (1978)]. Among them, 99mTc-labeled pyridoxylidene-isoleucine was actually subjected to clinical examination, and its utility as a hepatobiliary diagnostic agent has been highly evaluated.

As a result of the extensive study, it has been found that the complex formed from an N-pyridoxyl-α-amino acid and $^{99m}$Tc shows chemical and biological behaviors in mammals similar to those of the complex formed from the corresponding N-pyridoxylidene-α-amino acid and $^{99m}$Tc. For instance, their chromatographic behavior and distribution in mammalian bodies are extremely similar to each other. Advantageously, an N-pyridoxyl-α-amino acid is more stable than the corresponding N-pyridoxylidene-α-amino acid within a wider range of pH, and therefore the former is more suitable for a carrier than the latter. This invention is based on the above finding.

According to the present invention, there is provided a non-radioactive carrier to be used in diagnosis in nuclear medicine which comprises an N-pyridoxyl-α-amino acid of the formula:

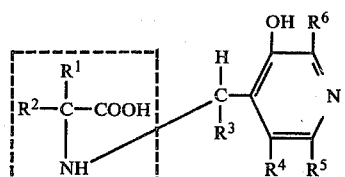

(I)

wherein $R^1$ and $R^2$ are each an atom or an atomic group present in the α-amino acid residue encompassed by the dotted line and $R^3$, $R^4$, $R^5$ and $R^6$ are each a hydrogen atom, a halogen atom (e.g. chlorine, bromine, iodine, fluorine), a $C_1$-$C_{10}$ alkyl group (e.g. methyl, ethyl, propyl, butyl, pentyl, octyl) or a $C_1$-$C_{10}$ alkyl group substituted with at least one hydrophilic group or its salt, and a reducing agent for pertechnetate.

There is also provided a radioactive diagnostic agent, particularly useful for examination of hepatobiliary ducts, which comprises $^{99m}$Tc in the form of pertechnetate and the non-radioactive carrier.

Among the said symbols, $R^1$ and $R^2$ can each represent any atom or atomic group which may be present in the α-amino acid residue encompassed by the dotted line. Examples of such atom and atomic group are hydrogen, $C_1$-$C_{10}$ alkyl, $C_1$-$C_{10}$ alkyl substituted with at least one of amino, imino, nitro, hydroxyl, mercapto, $C_1$-$C_{10}$ alkoxy, $C_1$-$C_{10}$ alkylthio, carboxyl, oxo, thio, carbonamido, phenyl, etc., amino, imino, nitro, hydroxyl, mercapto, $C_1$-$C_{10}$ alkoxy, $C_1$-$C_{10}$ alkylthio, carboxyl, oxo, thio, carbonamido, phenyl, etc. Thus, the said atom or atomic group may be any one which is present in alanine, arginine, asparagine, aspartic acid, cysteine, cystine, glutamine, glutamic acid, glycine, histidine, hydroxylysine, hydroxyproline, isoleucine, leucine, lysine, methionine, norleucine, norvaline, ornithine, phenylalanine, proline, serine, taurine, threonine, thyrosine, tryptophan, tyrosine, valine, etc. As the hydrophilic group which may be present on the alkyl group represented by $R^3$, $R^4$, $R^5$ or $R^6$, there are exemplified —$SO_3H$, —$SO_3M$, —$OSO_3H$, —$OSO_3M$, —COOM, —$NR_3X$, —COOH, —$NH_2$, —CN, —OH, —$NHCONH_2$, —$(OCH_2CH_2)_n$—, etc. (in which M is an alkali metal atom or an ammonium group, X is a halogen atom, R is a $C_1$-$C_{10}$ alkyl group and n is an optional integer).

The non-radioactive carrier of the present invention comprises as the essential components at least one of the N-pyridoxyl-α-amino acids of the formula (I) and their salts and at least one of the reducing agents for pertechnetate.

The N-pyridoxyl-α-amino acids of the formula (I) may be manufactured by various procedures, among which a typical example is representable by the formulas:

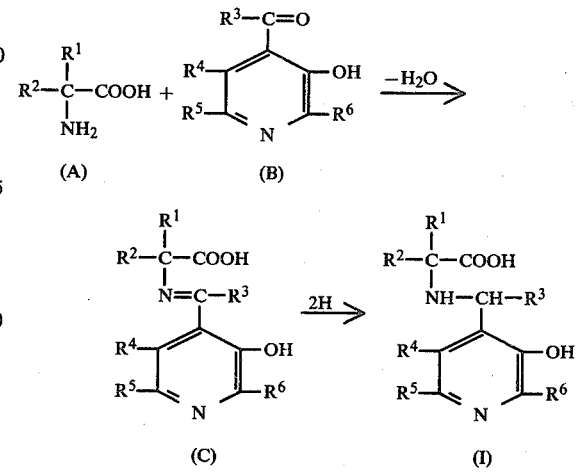

wherein $R^1$, $R^2$, $R^3$, $R^4$, $R^5$ and $R^6$ are each as defined above. Namely, the α-amino acid (A) and the pyridylketone (B) are condensed, followed by hydrogenation of the resulting Schiff base (C) to give the pyridoxyl-α-amino acid (I). The condensation is usually carried out in the presence of a base such as potassium hydroxide in an inert solvent such as anhydrous methanol, and the subsequent hydrogenation may be accomplished by catalytic hydrogenation in a conventional manner [J. Am. Chem. Soc., 70, 3429 (1948)].

Among various N-pyridoxyl-α-amino acids (I), preferred are those wherein $R^3$ and $R^5$ are each hydrogen, $R^4$ is hydroxymethyl and $R^6$ is methyl. While $R^1$ and $R^2$ can each represent any atom or atomic group which exists in the residue of a natural or artificial α-amino acid encompassed by the dotted line in the formula (I), their preferred examples are hydrogen, lower alkyl (e.g. methyl, isopropyl, 1-methylpropyl, 2-methylpropyl), carboxy(lower)alkyl (e.g. 2-carboxyethyl), hydroxy(lower)alkyl (e.g. hydroxymethyl, 1-hydroxyethyl), phenyl(lower)alkyl (e.g. benzyl), hydroxyphenyl(lower)alkyl (e.g. 4-hydroxybenzyl), etc. The term "lower" is intended to mean an atomic group having not more than 8 carbon atoms.

One of typical examples of the N-pyridoxyl-α-amino acids (I) is an N-pyridoxyl-tryptophan derivative of the formula:

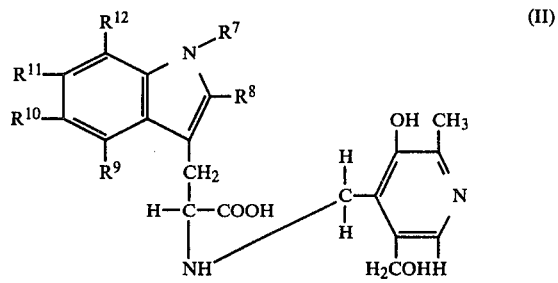

wherein $R^7$, $R^8$, $R^9$, $R^{10}$, $R^{11}$ and $R^{12}$ are each a hydrogen atom, a halogen atom, a $C_1$-$C_5$ alkyl group or a $C_1$-$C_5$ alkyl group substituted with at least one hydrophilic group. Particularly preferred is one of the formula (II) wherein $R^7$, $R^8$, $R^9$, $R^{11}$ and $R^{12}$ are each hydrogen and $R^{10}$ is hydrogen or methyl.

Depending upon the kinds of $R^1$, $R^2$ and $R^3$, the carbon atoms to which those groups are attached may be asymmetric carbon atoms. In such case, there may be present four kinds of optical isomers or diastereomers, i.e. RR—, RS—, SR—and SS—forms. Any of these isomers and their mixtures can be equally used in the non-radioactive carrier of the invention.

Examples of the salts of the N-pyridoxyl-α-amino acids (I) are the salts formed with organic or inorganic cations such as sodium ion, potassium ion and ammonium ion, the salts formed with inorganic acids such as hydrochloric acid, nitric acid, sulfuric acid and phosphoric acid, the salts formed with organic acids such as acetic acid and oxalic acid, etc.

As the reducing agent for pertechnetate, there may be used any stannous salt chosen from stannous halides (e.g. stannous chloride, stannous fluoride), stannous sulfate, stannous nitrate, stannous acetate, stannous citrate, stannous tartrate, etc. Any other reducing agent which can convert heptavalent technetium into any lower valent technetium is also usable insofar as its administration to mammals does not produce any material toxicity. Examples of such other reducing agent are cuprous salts, sodium borohydride, lithium aluminum hydride, etc.

On preparation of the non-radioactive carrier of the invention, the said essential components, i.e. the N-pyridoxyl-α-amino acid (I) or its salt and the reducing agent for pertechnetate, may be mixed in an optional order. The non-radioactive carrier may be in a solid preparation form such as powder or lyophilized powder or in a liquid preparation form such as aqueous solution. The pH of the non-radioactive carrier is not limitative, but it is preferred to adjust the pH within a range of about 3 to 10, particularly of about 6 to 9, for instance, by the use of an acid (e.g. hydrochloric acid) or an alkali (e.g. sodium hydroxide).

In addition to the said essential components, the non-radioactive carrier may include any conventional additive such as an antioxidant (e.g. ascorbic acid, erythorbic acid, gentisic acid), an isotonization agent (e.g. sodium chloride) or a preservative (e.g. benzyl alcohol).

The molar ratio of the N-pyridoxyl-α-amino acid (I) or its salt and the reducing agent for pertechnetate in the non-radioactive carrier is usually within a range of 1 to 100, preferably of 3 to 30. The reducing agent may be used in a sufficient amount to reduce $^{99m}$Tc in the form of pertechnetate present in the $^{99m}$Tc-labeled radioactive diagnostic agent prepared by the use of the non-radioactive carrier. When the stability of the non-radioactive carrier is taken into consideration, the reducing agent may be employed in such an amount as being left at a concentration of 0.1 to 5 mmol/L after the preparation of the $^{99m}$Tc-labeled radioactive diagnostic agent.

For preparation of the $^{99m}$Tc-labeled radioactive diagnostic agent, $^{99m}$Tc in the form of pertechnetate may be contacted with the non-radioactive carrier. $^{99m}$Tc in the form of pertechnetate is used normally in its aqueous solution, which may include additionally any conventional additive such as a preservative (e.g. benzyl alcohol) or an isotonization agent (e.g. sodium chloride). While the concentration of $^{99m}$Tc in the aqueous solution as the $^{99m}$Tc-labeled radioactive diagnostic agent is not particularly limited, it should have such a concentration as can afford a sufficient radioactivity concentration for diagnosis of hepatobiliary ducts, preferably from about 0.1 to 50 mCi in about 0.5 to 5.0 ml at the time of administration.

As the result of the combination of the non-radioactive carrier in an aqueous solution form with an aqueous solution comprising $^{99m}$Tc in the form of pertechnetate, there is prepared the $^{99m}$Tc-labeled radioactive diagnostic agent in situ.

The non-radioactive carrier of the present invention has the following advantageous characteristics:

(1) The carrier is quite stable within a wide range of pH so that it can be stored for a long period of time after the preparation;

(2) The carrier can afford a $^{99m}$Tc-labeled radioactive diagnostic agent by a simple operation, for instance, by contacting an aqueous solution comprising $^{99m}$Tc in the form of pertechnetate therewith;

(3) The carrier is materially non-toxic, etc.

Further, the $^{99m}$Tc-labeled radioactive diagnostic agent prepared by the use of such carrier has the following meritorious features:

(a) The diagnostic agent is stable for a sufficiently long period of time after the preparation;

(b) the labeling efficiency of $^{99m}$Tc is extremely high (e.g. 98% or more);

(c) when intravenously administered, the diagnostic agent is smoothly taken into the liver, transferred to the gall bladder and then passed through the bile duct to the small intestine so that the inspection can be accomplished within a short period of time;

(d) the radiation exposure for patients is much reduced in comparison with $^{131}$I-labeled radioactive hepatobiliary diagnostic agents;

(e) the toxicity is quite low, etc.

The $^{99m}$Tc-labeled radioactive diagnostic agent may be administered to patients in an amount sufficient to produce radioactivity necessary for examination of hepatobiliary ducts by an appropriate route. For instance, the intravenous administration of the $^{99m}$Tc-labeled radioactive diagnostic agent of about 1 to 3 ml in volume having a radioactivity of about 1 to 5 mCi to a patient is quite suitable for hepatobiliary diagnosis.

Practical and presently preferred embodiments of the present invention are illustratively shown in the following Examples.

EXAMPLE 1

Preparation of a non-radioactive carrier by the use of N-pyridoxyl-L-tryptophan and stannous chloride (hereinafter referred to as "PLTSnA")

Into sterilized water containing no pyrogen substance, germfree nitrogen gas was introduced to eliminate oxygen dissolved therein. Into the resulting water (500 ml), L-(+)-ascorbic acid (334 mg) was dissolved, and N-pyridoxyl-L-tryptophan [J. Am. Chem. Soc., 70, 3429 (1948)] (1599 mg) was suspended therein. To the resultant suspension while stirring, 2 N sodium hydroxide solution (2.3 ml) was gradually added to make the suspending particles dissolved completely. The resulting solution was adjusted to a pH of about 7 with 2 N hydrochloric acid, and anhydrous stannous chloride (48 mg) was dissolved therein while stirring. The resultant solution was adjusted to pH 8.20 with 2 N sodium hydroxide solution and/or 2 N hydrochloric acid, whereby a colorless, transparent solution, i.e. the non-radioactive carrier "PLTSnA," was obtained. The non-radioactive carrier "PLTSnA" (1 ml) was filled in a vial through a filter of 0.22μ in pore size in nitrogen atmosphere.

EXAMPLE 2

Preparation of a $^{99m}$Tc-labeled radioactive diagnostic agent using the non-radioactive carrier "PLTSnA" (hereinafter referred to as "Tc-(PLTSnA)")

In a vial flushed with nitrogen gas, the non-radioactive carrier "PLTSnA" (1.0 ml) was admixed with a physiological saline solution containing $^{99m}$Tc (10 mCi) in the form of sodium pertechnetate (1.0 ml) and stirred well. The vial was heated in a bath of boiling water for 5 minutes and then cooled in a water bath at room temperature to make a colorless, transparent solution as the $^{99m}$Tc-labeled radioactive diagnostic agent "Tc-(PLTSnA)."

The $^{99m}$Tc-labeled radioactive diagnostic agent "Tc-(PLTSnA)" as prepared above was subjected to thin layer chromatography using a silica gel thin layer plate and a mixture of methyl ethyl ketone, methanol and 2 M potassium chloride solution (10:9:1 by volume) as a developing solvent. Scanning with a radiochromatogram scanner revealed the presence of a single spot having radioactivity at Rf=0.62, and any other radioactive peak was not recognized.

Since, in the above chromatography system, $^{99m}$Tc in the form of pertechnetate is to be developed to Rf=0.96 and a $^{99m}$Tc-labeled tin colloid is to be retained at the original point, the presence of a single radioactive spot at Rf=0.62 means that the labeling efficiency is 100%.

EXAMPLE 3

Distribution of the $^{99m}$Tc-labeled radioactive diagnostic agent "Tc-(PLTSnA)" in the organs of rats The $^{99m}$Tc-labeled radioactive diagnostic agent "Tc-(PLTSnA)" (0.2 ml) was administered intravenously to S.D. (Sprague-Dawley) strain female rats. Five minutes or 1 hour after the administration, the animals were sacrificed, and various organs were taken out and subjected to measurement of radioactivity. The results are shown in Table 1.

TABLE 1

Distribution of Tc—(PLTSnA) in organs of rats (% to radioactivity administered; average for 5 animals)

| Organs | After administration | |
|---|---|---|
| | 5 minutes | 1 hour |
| Liver | 10.76 | 0.79 |
| Small intestine | 69.82 | 94.13 |
| Large intestine | 0.49 | 0.07 |
| Stomach | 0.11 | 0.08 |
| Spleen | 0.04 | 0.04 |
| Lung | 0.31 | 0.07 |
| Heart | 0.07 | 0.02 |
| Kidneys | 0.98 | 0.21 |
| Blood (1 ml)* | 0.18 | 0.021 |
| Carcass | 14.12 | 1.26 |
| Bladder (Urine) | 0.78 | 2.85 |

Note: *Body weight normalized to 200 grams.

The above results show that the $^{99m}$Tc-labeled radioactive diagnostic agent "Tc-(PLTSnA)" is useful as an excellent radioactive diagnostic agent for examination of hepatobiliary ducts.

EXAMPLE 4

Stability of the non-radioactive carrier "PLTSnA"

The non-radioactive carrier "PLTSnA" as prepared in Example 1 was stored at 3° to 6° C. under the state of prevention from light for a period of 50 or 100 days. By the use of the resulting non-radioactive carrier, a $^{99m}$Tc-labeled radioactive diagnostic agent "Tc-(PLTSnA)" was prepared as in Example 2. The labeling efficiency was confirmed to be 100% in both cases (i.e. after 50 days storage and after 100 days storage). The distributions in the organs of rats when tested as in Example 3 are shown in Table 2 wherein the values indicate those 1 hour after the administration.

TABLE 2

Distribution of Tc—(PLTSnA) in organs of rats (% to radioactivity administered; average for 5 animals)

| Organs | After preparation | |
|---|---|---|
| | 50 days | 100 days |
| Liver | 0.81 | 0.78 |
| Small intestine | 93.72 | 93.98 |
| Large intestine | 0.04 | 0.03 |
| Stomach | 0.09 | 0.08 |
| Spleen | 0.06 | 0.07 |
| Lung | 0.08 | 0.07 |
| Heart | 0.02 | 0.02 |
| Kidneys | 0.23 | 0.25 |
| Blood (1 ml)* | 0.023 | 0.024 |
| Carcass | 1.68 | 1.50 |

TABLE 2-continued

Distribution of Tc—(PLTSnA) in organs of rats (% to radioactivity administered; average for 5 animals)

| Organs | After preparation | |
|---|---|---|
| | 50 days | 100 days |
| Bladder (Urine) | 2.92 | 2.89 |

Note: *Body weight normalized to 200 grams.

From the above results, it is understood that the non-radioactive carrier "PLTSnA" is stable even after the storage at 3° to 6° C. for a period of 100 days or more.

EXAMPLE 5

Stability of the $^{99m}$Tc-labeled radioactive diagnostic agent "Tc-(PLTSnA)"

The $^{99m}$Tc-labeled radioactive diagnostic agent "Tc-(PLTSnA)" as prepared in Example 2 was stored at room temperature under the state of prevention from light for 24 or 48 hours. Then, the distribution of the resulting diagnostic agent in the organs of rats was examined as in Example 3. The results are shown in Table 3 wherein the values indicate those 1 hour after the administration.

TABLE 3

Distribution of Tc—(PLTSnA) in organs of rats (% to radioactivity administered; average for 5 animals)

| Organs | After preparation | |
|---|---|---|
| | 24 hours | 48 hours |
| Liver | 0.89 | 0.82 |
| Small intestine | 93.31 | 93.62 |
| Large intestine | 0.06 | 0.05 |
| Stomach | 0.09 | 0.07 |
| Spleen | 0.05 | 0.06 |
| Lung | 0.09 | 0.08 |
| Heart | 0.03 | 0.04 |
| Kidneys | 0.27 | 0.29 |
| Blood (1 ml)* | 0.026 | 0.024 |
| Carcass | 1.86 | 1.76 |
| Bladder (Urine) | 2.98 | 2.88 |

Note: *Body weight normalized to 200 grams.

From the above results, it is understood that the $^{99m}$Tc-labeled radioactive diagnostic agent "Tc-(PLTSnA)" is stable even after stored at room temperature for 48 hours or more. Since the half life of $^{99m}$Tc is about 6 hours, the assurance of the stability for a period of about 24 hours is sufficient for the practical use of the $^{99m}$Tc-labeled radioactive diagnostic agent.

EXAMPLE 6

Preparation of non-radioactive carriers using the N-pyridoxyl-α-amino acids (I) other than N-pyridoxyl-L-tryptophan In the same manner as in Example 1 but using N-pyridoxyl-L-isoleucine, N-pyridoxyl-L-phenylalanine or N-pyridoxyl-DL-5-methyltryptophan prepared by a conventional procedure [J. Am. Chem. Soc., 70, 3429 (1948)] in place of N-pyridoxyl-L-tryptophan, there was prepared the non-radioactive carrier "PLISnA," "PLPSnA" or "PDLMTSnA."

EXAMPLE 7

Preparation of a $^{99m}$Tc-labeled radioactive diagnostic agents using the non-radioactive carriers obtained by the use of the N-pyridoxyl-α-amino acids (I) other than N-pyridoxyl-tryptophan In the same manner as in Example 2 but using the non-radioactive carrier "PLISnA," "PLPSnA" or "PDLMTSnA" in place of the non-radioactive carrier "PLTSnA," there was prepared the $^{99m}$Tc-labeled radioactive diagnostic agent "Tc-(PLISnA)," "Tc-(PLPSnA)" or "Tc-(PDLMTSnA)" as a colorless, transparent solution.

EXAMPLE 8

Distribution of the $^{99m}$Tc-labeled radioactive diagnostic agents in the organs of rats In the same manner as in Example 3 but using the $^{99m}$Tc-labeled radioactive diagnostic agent "Tc-(PLISnA)," "Tc-(PLPSnA)" or "Tc-(PDLMTSnA)" in place of the $^{99m}$Tc-labeled radioactive diagnostic agent "Tc-(PLTSnA)," the distribution in the organs of rats 1 hour after the administration was examined. The results are shown in Table 4.

TABLE 4

Distribution of Tc—(PLISnA), Tc—(PLPSnA) and Tc—(PDLMTSnA) in organs of rats (% to radioactivity administered, average for 5 animals)

| Organs | Tc—(PLISnA) | Tc—(PLPSnA) | Tc—(PDLMTSnA) |
|---|---|---|---|
| Liver | 0.69 | 4.49 | 1.26 |
| Small intestine | 84.82 | 81.76 | 93.00 |
| Large intestine | 0.04 | 0.04 | 0.04 |
| Stomach | 0.03 | 0.04 | 0.06 |
| Spleen | 0.02 | 0.03 | 0.04 |
| Lung | 0.08 | 0.08 | 0.07 |
| Heart | 0.03 | 0.02 | 0.02 |
| Kidneys | 0.89 | 1.02 | 0.25 |
| Blood (1 ml)* | 0.038 | 0.042 | 0.028 |
| Carcass | 2.00 | 2.03 | 3.17 |
| Bladder (Urine) | 11.00 | 9.91 | 1.70 |

Note: *Body weight normalized to 200 grams.

From the above results, it is understood that the $^{99m}$Tc-labeled radioactive diagnostic agents are all useful for examination of hepatobiliary ducts.

EXAMPLE 9

Stability of the non-radioactive carriers "PLISnA," "PLPSnA" and "PDLMTSnA"

In the same manner as in Example 4, the stability of the non-radioactive carriers "PLISnA," "PLPSnA" and "PDLMTSnA" was examined. As the results, it was confirmed that they are stable even after stored for a period of 100 days or more.

EXAMPLE 10

Stability of the $^{99m}$Tc-labeled radioactive diagnostic agents "Tc-(PLISnA)", "Tc-(PLPSnA)" and "Tc-(PDLMTSnA)"

In the same manner as in Example 5, the stability of the $^{99m}$Tc-labeled radioactive diagnostic agents "Tc-(PLTSnA)," "Tc-(PLTSnA)" and "Tc-(PDLMTSnA)" was examined. As the results, it was confirmed that they are stable even after stored for a period of 48 hours or more.

EXAMPLE 11

Toxicity of the non-radioactive diagnostic agents

In the same manner as in Example 1 or 6 but using the materials other than water in amounts of 2 times, there were prepared non-radioactive carriers having 2 fold concentrations in comparison with the concentrations of the non-radioactive carriers as prepared in Example 1 or 6.

The resulting non-radioactive carriers were intravenously administered to groups of SD strain male rats, groups of SD strain female rats, groups of ICR strain male mice and groups of ICR strain female mice, each group consisting of 10 animals, at a dose of 1 ml per 100 g of body weight. (This dose corresponds to 2400 times the normal dose to human beings.) Separately, the same volume of physiological saline solution as above (per unit of body weight) was intravenously administered to the same groups of animals as above for the control.

For 10 days after the administration, the animals were fed, and the change of body weight was daily recorded. No significant reference was recognized between the drug administered groups and the control groups. Then, all the animals were sacrificed and subjected to observation of the abnormality in various organs. But, no abnormality was seen in any of the animals.

From the above results, it may be said that the toxicity of the non-radioactive carrier according to this invention is extremely low.

What is claimed is:

1. A non-radioactive carrier comprising an N-pyridoxyl-α-amino acid of the formula:

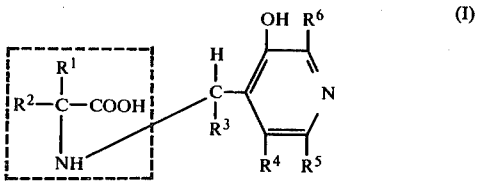

wherein $R^1$ and $R^2$ are each an atom or an atomic group present in the α-amino acid residue encompassed by the dotted line and $R^3$, $R^4$, $R^5$ and $R^6$ are each a hydrogen atom, a halogen atom, a $C_1$-$C_{10}$ alkyl group or a $C_1$-$C_{10}$ alkyl group substituted with at least one hydrophilic group or its salt, and a reducing agent for pertechnetate.

2. The non-radioactive carrier according to claim 1, wherein the N-pyridoxyl-α-amino acid is the one of the formula (I) wherein $R^3$ and $R^5$ are each hydrogen, $R^4$ is hydroxymethyl and $R^6$ is methyl.

3. The non-radioactive carrier according to claim 1, wherein the N-pyridoxyl-α-amino acid is the one of the formula (I) wherein $R^2$, $R^3$ and $R^5$ are each hydrogen, $R^4$ is hydroxymethyl and $R^6$ is methyl.

4. The non-radioactive carrier according to claim 1, wherein the N-pyridoxyl-α-amino acid is the one of the formula (I) wherein $R^1$ is hydrogen, methyl, isopropyl, 1-methylpropyl, 2-methylpropyl, 2-carboxyethyl, hydroxymethyl, 1-hydroxyethyl, benzyl or 4-hydroxybenzyl, $R^2$, $R^3$ and $R^5$ are each hydrogen, $R^4$ is hydroxymethyl and $R^6$ is methyl.

5. The non-radioactive carrier according to claim 1, wherein the N-pyridoxyl-α-amino acid is an N-pyridoxyl-tryptophan derivative of the formula:

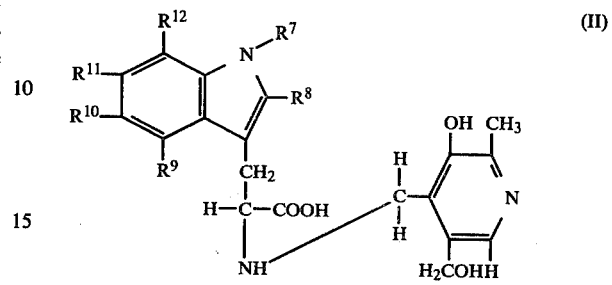

wherein $R^7$, $R^8$, $R^9$, $R^{10}$, $R^{11}$ and $R^{12}$ are each a hydrogen atom, a halogen atom, a $C_1$-$C_5$ alkyl group or a $C_1$-$C_5$ alkyl group substituted with at least one hydrophilic group.

6. The non-radioactive carrier according to claim 5, wherein the N-pyridoxyl-tryptophan derivative is the one of the formula (II) wherein $R^7$, $R^8$, $R^9$, $R^{11}$ and $R^{12}$ are each hydrogen and $R^{10}$ is hydrogen or methyl.

7. The non-radioactive carrier according to claim 1, wherein the reducing agent for pertechnetate is a stannous salt.

8. The non-radioactive carrier according to claim 1, wherein the reducing agent for pertechnetate is contained in an amount of 0.001 to 1 mol per 1 mol of the N-pyridoxyl-α-amino acid or its salt.

9. The non-radioactive carrier according to claim 1, which is in the form of aqueous solution.

10. The non-radioactive carrier according to claim 9, wherein the concentration of the N-pyridoxyl-α-amino acid or its salt is not less than 20 mmol/liter.

11. A $^{99m}$Tc-labeled radioactive diagnostic agent which comprises $^{99m}$Tc in the form of pertechnetate and the non-radioactive carrier comprising an N-pyridyl-α-amino acid of the formula:

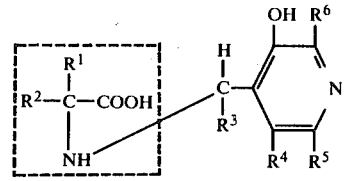

wherein $R^1$ and $R^2$ are each an atom or an atomic group present in the α-amino acid residue encompassed by the dotted line and $R^3$, $R^4$, $R^5$ and $R^6$ are each a hydrogen atom, a halogen atom, a $C_1$-$C_{10}$ alkyl group or a $C_1$-$C_{10}$ alkyl group substituted with at least one hydrophilic group or its salt, and a reducing agent for pertechnetate.

12. The $^{99m}$Tc-labeled radioactive diagnostic agent according to claim 11, prepared by contacting an aqueous solution containing $^{99m}$Tc, the radioactivity of which is 0.1 to 50 mCi in a volume of 0.5 to 5 ml aqueous solution at the time of administration, in the form of pertechnetate with the non-radioactive carrier.

* * * * *